United States Patent
Tanigawara et al.

(10) Patent No.: US 9,733,256 B2
(45) Date of Patent: Aug. 15, 2017

(54) COMBINED ANTICANCER DRUG SENSITIVITY-DETERMINING MARKER

(71) Applicants: KEIO UNIVERSITY, Minato-ku (JP); KABUSHIKI KAISHA YAKULT HONSHA, Minato-ku (JP)

(72) Inventors: Yusuke Tanigawara, Shinjuku-ku (JP); Akito Nishimuta, Shinjuku-ku (JP); Junya Tsuzaki, Shinjuku-ku (JP); Hiroyuki Takahashi, Minato-ku (JP)

(73) Assignees: KEIO UNIVERSITY, Minato-ku (JP); KABUSHIKI KAISHA YAKULT HONSHA, Minato-ku (JP)

( * ) Notice: Subject to any disclaimer, the term of this patent is extended or adjusted under 35 U.S.C. 154(b) by 0 days.

(21) Appl. No.: 14/379,945

(22) PCT Filed: Feb. 22, 2013

(86) PCT No.: PCT/JP2013/054488
§ 371 (c)(1),
(2) Date: Aug. 20, 2014

(87) PCT Pub. No.: WO2013/125675
PCT Pub. Date: Aug. 29, 2013

(65) Prior Publication Data
US 2015/0038522 A1 Feb. 5, 2015

(30) Foreign Application Priority Data
Feb. 23, 2012 (JP) .................................. 2012-037448

(51) Int. Cl.
*A61K 31/282* (2006.01)
*A61K 31/513* (2006.01)
(Continued)

(52) U.S. Cl.
CPC ....... *G01N 33/6848* (2013.01); *A61K 31/282* (2013.01); *A61K 31/513* (2013.01);
(Continued)

(58) Field of Classification Search
CPC ......... G01N 33/6848; G01N 33/57484; A61K 31/282; A61K 31/336; A61K 31/513
See application file for complete search history.

(56) References Cited

U.S. PATENT DOCUMENTS

2010/0292331 A1  11/2010  Mitchell et al.
2010/0323034 A1  12/2010  Tanigawara et al.
(Continued)

FOREIGN PATENT DOCUMENTS

WO  2009/096189  8/2009
WO  2009/096196  8/2009
(Continued)

OTHER PUBLICATIONS

Braun et al.; "Predictive Biomarkers of Chemotherapy Efficacy in Colorectal Cancer: Results From the UK MRC FOCUS Trial"; 2008; Journal of Clinical Oncology; 26(16): 2690-2698.*
(Continued)

*Primary Examiner* — Timothy Thomas
(74) *Attorney, Agent, or Firm* — Oblon, McClelland, Maier & Neustadt, L.L.P.

(57) ABSTRACT

To provide an anti-cancer agent sensitivity determination marker, which marker can determine whether or not the patient has a therapeutic response to the anti-cancer agent, and novel cancer therapeutic means employing the marker. The anti-cancer agent sensitivity determination marker, the anti-cancer agent including oxaliplatin or a salt thereof and fluorouracil or a salt thereof, contains one or more substances selected from among an amino-acid-metabolism-related substance, a nucleic-acid-metabolism-related sub-
(Continued)

stance, a substance in the pentose phosphate pathway, a substance in the glycolytic pathway, a substance in the TCA cycle, a polyamine-metabolism-related substance, 7,8-dihydrobiopterin, 6-phosphogluconic acid, butyric acid, triethanolamine, 1-methylnicotinamide, NADH, $NAD^+$, and a substance involved in the metabolism of any of these substances.

3 Claims, 3 Drawing Sheets

(51) Int. Cl.
*G01N 33/68* (2006.01)
*G01N 33/574* (2006.01)
*A61K 45/06* (2006.01)
*A61K 31/555* (2006.01)
*A61K 47/18* (2017.01)
*A61K 47/26* (2006.01)

(52) U.S. Cl.
CPC ............ *A61K 31/555* (2013.01); *A61K 45/06* (2013.01); *A61K 47/18* (2013.01); *A61K 47/183* (2013.01); *A61K 47/26* (2013.01); *G01N 33/57484* (2013.01); *G01N 2560/00* (2013.01); *G01N 2570/00* (2013.01); *G01N 2800/52* (2013.01); *Y10T 436/143333* (2015.01); *Y10T 436/147777* (2015.01); *Y10T 436/163333* (2015.01); *Y10T 436/173845* (2015.01); *Y10T 436/201666* (2015.01)

(56) References Cited

U.S. PATENT DOCUMENTS

2011/0003842 A1   1/2011   Tanigawara et al.
2012/0220618 A1*  8/2012   Tanigawara et al. ......... 514/283

FOREIGN PATENT DOCUMENTS

WO       2011/052750      5/2011
WO    WO 2011052750 A1 *  5/2011

OTHER PUBLICATIONS

International Search Report issued Jun. 4, 2013, in PCT/JP13/054488, filed Feb. 22, 2013.
Braun, M. S., et al., "Predictive Biomarkers of Chemotherapy Efficacy in Colorectal Cancer: Results From the UK MRC FOCUS Trial", Journal of Clinical Oncology, vol. 26, No. 16, pp. 2690-2698, 2008.
Akito Nishimura et. al., "Intracellular metabolite kinetics after 5-FU exposure by CE-TOFMS metabolome analysis", Cancer Research, May 2008, p. 2563.

* cited by examiner

Fig. 1

| | Metabolite | DLD1 | HCT116 | Ratio (HCT116/DLD-1) |
|---|---|---|---|---|
| Amino acid metabolism | Asp | 2.54 | 4.96 | 1.95 |
| | Gly | 1.20 | 1.94 | 1.62 |
| | Arg | 1.41 | 2.34 | 1.66 |
| | N-Acetyl-beta-alanine | 1.36 | 2.26 | 1.66 |
| | N-Acetylornithine | 1.21 | 2.00 | 1.65 |
| | N,N-Dimethylglycine | 2.09 | 1.28 | 0.61 |
| | 3-Methylhistidine | 1.63 | 1.07 | 0.65 |
| | $N^5$-Ethylglutamine | 1.63 | 1.06 | 0.65 |
| | gamma-Glu-Cys | 0 | 8.23 | ∞ |
| | beta-Ala-Lys | 1.36 | 4.28 | 3.15 |
| | Glutathione (GSH) | 24.80 | 3.80 | 0.15 |
| | Glu-Glu | 1.19 | 3.32 | 2.79 |
| | S-Lactoylglutathione | 0.95 | 2.27 | 2.39 |
| | Cysteine-glutathione | 0.36 | 0.20 | 0.55 |
| | Cadaverine | 0 | 3.65 | ∞ |
| | Cysteic acid | 2.16 | 3.42 | 1.58 |
| | 2-Aminoadipic acid | 1.30 | 2.00 | 1.54 |
| | gamma-Aminobutyric acid | 1.02 | 1.79 | 1.76 |
| Nucleotide metabolism | Guanosine | 1.00 | 3.47 | 3.46 |
| | CMP | 1.86 | 3.09 | 1.66 |
| | UMP | 1.37 | 2.93 | 2.14 |
| | 1-Methyladenosine | 1.78 | 2.88 | 1.62 |
| | UDP | 0.96 | 2.38 | 2.49 |
| | CTP | 1.01 | 2.07 | 2.04 |
| | dATP | 2.39 | 1.25 | 0.52 |
| | Adenine | 1.15 | 0.63 | 0.55 |
| Pentose phosphate pathway | Sedoheptulose 7-phosphate | 1.68 | 3.61 | 2.14 |
| | PRPP | 0.93 | 0.26 | 0.28 |
| Glycolysis | Dihydroxyacetone phosphate | 0.90 | 2.41 | 2.68 |
| | 2,3-Diphosphoglyceric acid | 0.82 | 1.54 | 1.86 |
| | Pyruvic acid | 1.52 | 2.64 | 1.74 |
| TCA cycle | Malic acid | 1.51 | 2.65 | 1.75 |
| Polyamine metabolism | $N^1$-Acetylspermine | 1.97 | 6.62 | 3.36 |
| | N-Acetylputrescine | 0 | 3.52 | ∞ |
| | $N^8$-Acetylspermidine | 0.82 | 3.26 | 3.97 |
| | Putrescine | 0.74 | 3.26 | 4.40 |
| | Spermine | 0.85 | 2.31 | 2.72 |
| | Spermidine | 0.54 | 1.84 | 3.39 |
| Others | 7,8-Dihydrobiopterin | 1.45 | 2.42 | 1.68 |
| | 6-Phosphogluconic acid | 0.82 | 1.61 | 1.95 |
| | Butyric acid | 2.69 | 1.53 | 0.57 |
| | Triethanolamine | 2.02 | 1.27 | 0.63 |
| | 1-Methylnicotinamide | 1.58 | 1.04 | 0.66 |
| | NADH | 0.44 | 0.70 | 1.57 |
| | $NAD^+$ | 0.30 | 0.64 | 2.12 |

Ratio of intracellular level after 24-hour 5-FU/L-OHP exposure to that of control group in each cell strain

COMBINED ANTICANCER DRUG SENSITIVITY-DETERMINING MARKER

This application is a National Stage of PCT/JP13/054488 filed Feb. 22, 2013 and claims the benefit of JP 2012-037448 filed Feb. 23, 2012.

TECHNICAL FIELD

The present invention relates to a marker for use in determination of the sensitivity of a cancer patient to an anti-cancer agent to be administered thereto, which marker can determine whether or not the cancer of the patient has a therapeutic response to the anti-cancer agent, and to application of the marker.

BACKGROUND ART

Anti-cancer agents have various types such as an alkylating agent, a platinum agent, an antimetabolite, an antitumor antibiotic, and an antitumor plant alkaloid. These anti-cancer agents are effective for some cancers but not effective for other cancers. Even when an anti-cancer agent has been confirmed to be effective for a certain cancer, the anti-cancer agent is effective for some patients and not effective for other patients, leading to interindividual differences. Whether or not a cancer of a specific patient has response to an anti-cancer agent is designated as sensitivity to the anti-cancer agent.

Oxaliplatin (L-OHP) is a platinum-based complex anti-cancer agent. Similar to cisplatin (CDDP) and carboplatin (CBDCA), which are other platinum-based complex anti-cancer agents, the action mechanism thereof is thought to be based on inhibition of DNA synthesis or protein synthesis via cross-linking with DNA bases. L-OHP exhibits anti-tumor effect on colorectal cancer, to which CDDP or CBDCA is ineffective, and shows different spectrum of anti-tumor activity from that of a precedent platinum-based complex anti-cancer agent. In the United States of America, L-OHP for use in combination with fluorouracil (5-FU)/levofolinate (LV) was approved as a first line therapy for metastatic colorectal cancer in January, 2004. In Japan, L-OHP was listed in the National Health Insurance price list in the case of combination use thereof with continuous infusional LV and 5-FU (FOLFOX4 regimen) for "advanced/recurrent colorectal cancer not amenable to curative surgical resection" in April, 2005. Until the early 1990's, 5-FU/LV regimen to advanced/recurrent colorectal cancer has provided a survival of 10 to 12 months. In contrast, a FOLFOX regimen combined with L-OHP results in a prolonged survival of 19.5 months (about twice the survival time). In August, 2009, an indication of L-OHP combined with continuous infusional 5-FU/LV to "postoperative adjuvant chemotherapy for colon cancer" was added to efficacy and effectiveness. Thus, L-OHP is a promising drug having an efficacy in an increased number of colorectal cancer patients.

Meanwhile, 5-FU is a fluoro-pyrimidine anti-cancer agent developed in 1957 and even now serves as a basic drug for use in the chemotherapy of gastrointestinal cancer. When incorporated into cancer cells, 5-FU exerts cytotoxic effect through a principle action mechanism of DNA synthesis inhibition induced by inhibition of thymidylate synthase (TS) by an active metabolite, fluorodeoxyuridine-5'-monophosphate (FdUMP), and another mechanism of RNA function inhibition by another active metabolite, 5-fluorouridine triphosphate (FUTP).

Meanwhile, clinical performance including survival rate attained by chemotherapy of advanced or metastatic colorectal cancer has been drastically improved through a combination therapy employing a key drug such as irinotecan (CPT-11) or L-OHP, which was developed in the 1990s, and a fluoro-pyrimidine drug such as 5-FU, which has been a main drug for the therapy of colorectal cancer. However, the response rate of such chemotherapy is as low as about 50%. That is, the chemotherapy is not effective for half of the patients to whom an anti-cancer agent has been administered with high risks such as serious adverse events. Thus, in order to provide an optimum regimen in cancer chemotherapy, there is urgent demand for establishing a marker for predicting the sensitivity of a patient to an anti-cancer agent, which marker enables determination of therapeutic response of individual patients (i.e., indication of a responder or non-responder).

Generally, the therapy schedule of cancer chemotherapy requires a long period of time. After repetition of several courses of chemotherapy while emergence of adverse events is monitored, attainment of a therapeutic effect and continuation of the therapy are assessed. The assessment requires a long period of time and high medical cost, and the adverse events have actually been observed to a certain degree. Thus, if there were means for predicting whether or not individual patients can receive the effect of chemotherapy before or in an early stage of the therapy, the burden of the patients and emergence of adverse events can be reduced or mitigated, leading to reduction in medical cost.

Large-scale prospective clinical trial (FOCUS trial) for investigating biomarkers that predict therapeutic response of advanced colorectal cancer patients to chemotherapy has revealed that only topoisomerase-1 (TopoI) exhibits weak relationship with the 5-FU/L-OHP combination therapy as an effect predicting factor (Non-Patent Document 1). This indicates that there has been established no technique that can reliably select a patient who is expected to be effectively treated through the 5-FU/L-OHP combination therapy. Therefore, there is keen demand for establishment of a biomarker that can predict the effect of the FOLFOX regimen employing a triplet combination of L-OHP/5-FU/LV or that can diagnose the therapeutic response to the FOLFOX regimen in an early stage. Also, in recent years, a modified FOLFOX therapy with use of bevacizumab has been established, and new combination therapies employing an antibody drug such as cetuximab or panitumumab, and a low-molecular-weight compound such as irinotecan or dasatinib are now clinically investigated. Therefore, a marker for determining sensitivity of a patient to an anti-cancer agent containing 5-FU and L-OHP, serving as key drugs of these therapies, have been more and more of importance.

CITATION LIST

Non-Patent Document

Non-Patent Document 1: J. Clin. Oncol. 26, 2690-2698 (2008)

SUMMARY OF THE INVENTION

Problems to be Solved by the Invention

An object of the present invention is to provide an anti-cancer agent sensitivity determination marker, which the marker can determine whether or not the patient has a therapeutic response to the anti-cancer agent. Another object is to provide novel cancer therapeutic means employing the marker.

Means for Solving the Problems

In order to attain the aforementioned objects, the present inventors have searched for an anti-cancer agent sensitivity determination marker by culturing human cancer cells, and comprehensively analyzing the intracellular metabolism behavior after exposure to 5-FU/L-OHP by means of a capillary electrophoresis time-of-flight mass spectrometer (CE-TOFMS). As a result, the inventors have found peaks attributed to substances which exhibit, after exposure to 5-FU/L-OHP, a considerable rise in intracellular level in 5-FU/L-OHP-high-sensitivity cells, the peaks being amino-acid-metabolism-related substances (Asp, Gly, Arg, N-acetyl-β-alanine, N-acetylornithine, cadaverine, cysteic acid, 2-aminoadipic acid, GABA (γ-aminobutyric acid), γ-Glu-Cys, β-Ala-Lys, Glu-Glu, and S-lactoylglutathione), nucleic-acid-metabolism-related substances (guanosine, CMP, UMP, 1-methyladenosine, UDP, and CTP), a substance in the pentose phosphate pathway (sedoheptulose 7-phosphate), a substance in the glycolytic pathway (dihydroxyacetone phosphate, 2,3-diphosphoglyceric acid and pyruvic acid), a substance in the TCA cycle (malic acid), polyamine-metabolism-related substances ($N^1$-acetylspermine, N-acetylputrescine, $N^8$-acetylspermidine, putrescine, spermine, and spermidine), 7,8-dihydrobiopterin, and 6-phosphogluconic acid. Further, the inventors have found peaks attributed to substances which exhibit, after exposure to 5-FU/L-OHP, a considerable rise in intracellular level in 5-FU/L-OHP-low-sensitivity cells, the peaks being amino-acid-metabolism-related substances (N,N-dimethylglycine, 3-methylhistidine, $N^5$-ethylglutamine, and glutathione), a nucleic-acid-metabolism-related substance (dATP), butyric acid, triethanolamine, and 1-methylnicotinamide. Also, the inventors have found peaks attributed to a substance which exhibits, after exposure to 5-FU/L-OHP, a considerable drop in intracellular level in 5-FU/L-OHP-high-sensitivity cells, the peak being an amino-acid-metabolism-related substance (cysteine-glutathione), a nucleic-acid-metabolism-related substance (adenine), and a substance in the pentose phosphate pathway (PRPP). Also, the inventors have found peaks attributed to a substance which exhibits, after exposure to 5-FU/L-OHP, a considerable drop in intracellular level in 5-FU/L-OHP-low-sensitivity cells, the peak being NADH and $NAD^+$. The inventors have also found that intracellular GABA level before the treatment with the drug is higher in low-sensitivity cells than in high-sensitivity cells.

In addition, the present inventors have comprehensively analyzed, by means of a CE-TOFMS, blood metabolites in blood samples of colorectal cancer patients. As a result, the inventors have found that a high blood GABA level is observed in patients who have poor therapeutic response to the mFOLFOX6-bevacizumab combination therapy.

On the basis of these findings, the inventors have carried out further studies, and have found that whether or not a cancer of a target cancer patient has a sensitivity to an anti-cancer agent can be determined through measuring, as an index, the levels of any of the metabolites contained in a bio-sample derived from the cancer patient; that screening of an anti-cancer agent sensitivity enhancer can be accomplished through employment of the levels (or variation in level) as an index; and that the therapeutic effect of the relevant anti-cancer agent can be drastically enhanced by use, in combination, of the anti-cancer agent sensitivity enhancer and the anti-cancer agent which is a sensitivity enhancement target of the enhancer. The present invention has been accomplished on the basis of these findings.

Accordingly, the present invention provides an anti-cancer agent sensitivity determination marker, the anti-cancer agent including oxaliplatin or a salt thereof and fluorouracil or a salt thereof, comprising one or more substances selected from among an amino-acid-metabolism-related substance, a nucleic-acid-metabolism-related substance, a substance in the pentose phosphate pathway, a substance in the glycolytic pathway, a substance in the TCA cycle, a polyamine-metabolism-related substance, 7,8-dihydrobiopterin, 6-phosphogluconic acid, butyric acid, triethanolamine, 1-methylnicotinamide, NADH, $NAD^+$, and a substance involved in the metabolism of any of these substances.

The present invention also provides a method for determining sensitivity of a specimen to an anti-cancer agent, the anti-cancer agent including oxaliplatin or a salt thereof and fluorouracil or a salt thereof, characterized in that the method comprises determining any of these substances present in the specimen.

The present invention also provides a kit for carrying out the method for determining sensitivity of a specimen to an anti-cancer agent, the anti-cancer agent including oxaliplatin or a salt thereof and fluorouracil or a salt thereof, characterized in that the kit comprises a protocol for determining any of these substances present in the specimen.

The present invention also provides an anti-cancer agent sensitivity enhancer screening method, the anti-cancer agent including oxaliplatin or a salt thereof and fluorouracil or a salt thereof, the method comprising employing variation in expression of any of these substances as an index.

The present invention also provides an anti-cancer agent sensitivity enhancer, the anti-cancer agent including oxaliplatin or a salt thereof and fluorouracil or a salt thereof, the enhancer being selected through the screening method.

The present invention also provides a cancer therapy composition comprising, in combination, the anti-cancer agent sensitivity enhancer and an anti-cancer agent which includes oxaliplatin or a salt thereof and fluorouracil or a salt thereof.

Effects of the Invention

According to the anti-cancer agent sensitivity determination marker of the present invention, the therapeutic response of a patient to an anti-cancer agent can be correctly appropriately determined before the therapy or in an early stage after start of the therapy. As a result, an anti-cancer agent having higher therapeutic effect can be selected, and progression of cancer and aggravation of side effects, which would otherwise result from continuous administration of an anti-cancer agent exerting no expected therapeutic effect, can be prevented. Thus, reductions can be expected in suffering of the patient and medical cost. In addition, when the marker of the present invention is used, a drug which can promote anti-cancer agent sensitivity can be selected through screening. Thus, through employment, in combination, of the target anti-cancer agent and an anti-cancer agent sensitivity enhancer to the anti-cancer agent, the expected cancer therapeutic effect can be drastically enhanced. The assay reagent of the present invention containing the anti-cancer agent sensitivity determination marker is useful as an anti-cancer agent sensitivity determination reagent.

BRIEF DESCRIPTION OF THE DRAWINGS

FIG. 1 A table showing intracellular metabolite levels in DLD-1 cells and in HCT 116 cells, after 24-hour exposure to 5-FU/L-OHP.

MODES FOR CARRYING OUT THE INVENTION

Figure 2:
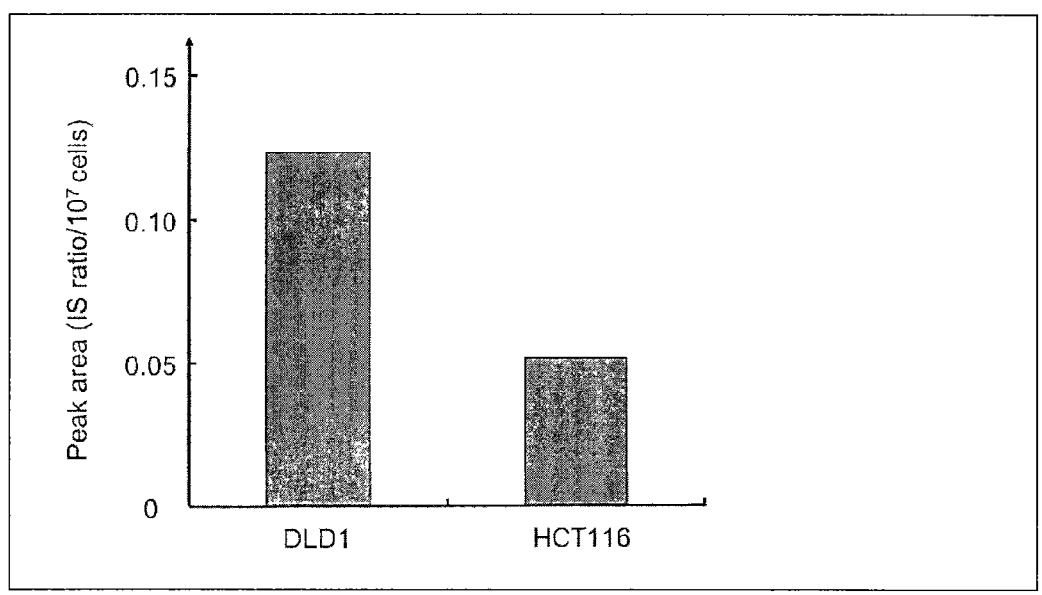
FIG. 2 A graph showing intracellular GABA levels in DLD-1 cells and in HCT 116 cells, before drug treatment.

One member of the anti-cancer agent sensitivity determination marker of the present invention is a substance involved in amino acid metabolism (also called an amino-acid-metabolism-related substance). The substance encompasses all the substances that can vary the amino-acid-metabolism-related substance level in a metabolic system. Examples of such metabolism-related substances include a substance which promotes metabolism to the amino-acid-metabolism-related substance, a substance which inhibits metabolism to the amino-acid-metabolism-related substance, a substance which promotes metabolism from the amino-acid-metabolism-related substance, and a substance which inhibits metabolism from the amino-acid-metabolism-related substance. Of these, Asp, Gly, Arg, N-acetyl-β-alanine, N-acetylornithine, cadaverine, cysteic acid, 2-aminoadipic acid, GABA (γ-aminobutyric acid), γ-Glu-Cys, β-Ala-Lys, Glu-Glu, S-lactoylglutathione, N,N-dimethylglycine, 3-methylhistidine, $N^5$-ethylglutamine, glutathione, and cysteine-glutathione are preferred, with cadaverine, γ-Glu-Cys, β-Ala-Lys, Glu-Glu, S-lactoylglutathione, glutathione, and GABA being particularly preferred.

Another member of the anti-cancer agent sensitivity determination marker of the present invention is a substance involved in nucleic acid metabolism (also called a nucleic-acid-metabolism-related substance). The substance encompasses all the substances that can vary the nucleic-acid-metabolism-related substance level. Examples of such metabolism-related substances include a substance which promotes metabolism to the nucleic-acid-metabolism-related substance, a substance which inhibits metabolism to the nucleic-acid-metabolism-related substance, a substance which promotes metabolism from the nucleic-acid-metabolism-related substance, and a substance which inhibits metabolism from the nucleic-acid-metabolism-related substance. Of these, guanosine, CMP, UMP, 1-methyladenosine, UDP, CTP, dATP, and adenine are preferred, with guanosine, UMP, UDP, and CTP being particularly preferred.

Another member of the anti-cancer agent sensitivity determination marker of the present invention is a substance involved in the pentose phosphate pathway (also called a substance in the pentose phosphate pathway). The substance encompasses all the substances that can vary the substance in the pentose phosphate pathway level. Examples of such substances include a substance which promotes metabolism to a substance in the pentose phosphate pathway, a substance which inhibits metabolism to a substance in the pentose phosphate pathway, a substance which promotes metabolism from a substance in the pentose phosphate pathway, and a substance which inhibits metabolism from a substance in the pentose phosphate pathway. Of these, sedoheptulose 7-phosphate and PRPP are particularly preferred.

Another member of the anti-cancer agent sensitivity determination marker of the present invention is a substance involved in glycolytic pathway (also called a substance in the glycolytic pathway). The substance encompasses all the substances that can vary the substance in the glycolytic pathway level. Examples of such substances include a substance which promotes metabolism to a substance in the glycolytic pathway, a substance which inhibits metabolism to a substance in the glycolytic pathway, a substance which promotes metabolism from a substance in the glycolytic pathway, and a substance which inhibits metabolism from a substance in the glycolytic pathway. Of these, dihydroxyacetone phosphate, 2,3-diphosphoglyceric acid, and pyruvic acid are preferred, with dihydroxyacetone phosphate being particularly preferred.

Another member of the anti-cancer agent sensitivity determination marker of the present invention is a substance involved in TCA cycle (also called a substance in the TCA cycle). The substance encompasses all the substances that can vary the substance in the TCA cycle level. Examples of such substances include a substance which promotes metabolism to a substance in the TCA cycle, a substance which inhibits metabolism to a substance in the TCA cycle, a substance which promotes metabolism from a substance in the TCA cycle, and a substance which inhibits metabolism from a substance in the TCA cycle. Of these, malic acid is particularly preferred.

Another member of the anti-cancer agent sensitivity determination marker of the present invention is a substance involved in polyamine metabolism (also called a polyamine-metabolism-related substance). The substance encompasses all the substances that can vary the polyamine-metabolism-related substance level. Examples of such metabolism-related substances include a substance which promotes metabolism to a polyamine-metabolism-related substance, a substance which inhibits metabolism to a polyamine-metabolism-related substance, a substance which promotes metabolism from a polyamine-metabolism-related substance, and a substance which inhibits metabolism from a polyamine-metabolism-related substance. Of these, $N^1$-acetylspermine, N-acetylputrescine, $N^8$-acetylspermidine, putrescine, spermine, and spermidine are particularly preferred.

Another member of the anti-cancer agent sensitivity determination marker of the present invention is 7,8-dihydrobiopterin or a substance involved in 7,8-dihydrobiopterin metabolism (also called a 7,8-dihydrobiopterin-metabolism-related substance). The substance encompasses 7,8-dihydrobiopterin and all the substances that can vary the 7,8-dihydrobiopterin level in the metabolism thereof. Examples of such metabolism-related substances include a substance which promotes metabolism to 7,8-dihydrobiopterin, a substance which inhibits metabolism to 7,8-dihydrobiopterin, a substance which promotes metabolism from 7,8-dihydrobiopterin, and a substance which inhibits metabolism from 7,8-dihydrobiopterin. Of these, 7,8-dihydrobiopterin is particularly preferred.

Another member of the anti-cancer agent sensitivity determination marker of the present invention is 6-phosphogluconic acid or a substance involved in 6-phosphogluconic acid metabolism (also called a 6-phosphogluconic-acid-metabolism-related substance). The substance encompasses 6-phosphogluconic acid and all the substances that can vary the 6-phosphogluconic acid level in the metabolism thereof. Examples of such metabolism-related substances include a substance which promotes metabolism to 6-phosphogluconic acid, a substance which inhibits metabolism to 6-phosphogluconic acid, a substance which promotes metabolism from 6-phosphogluconic acid, and a substance which inhibits metabolism from 6-phosphogluconic acid. Of these, 6-phosphogluconic acid is particularly preferred.

Another member of the anti-cancer agent sensitivity determination marker of the present invention is butyric acid or a substance involved in butyric acid metabolism (also called a butyric-acid-metabolism-related substance). The substance encompasses butyric acid and all the substances that can vary the butyric acid level in the metabolism thereof. Examples of such metabolism-related substances include a substance which promotes metabolism to butyric acid, a substance which inhibits metabolism to butyric acid, a substance which promotes metabolism from butyric acid, and a substance which inhibits metabolism from butyric acid. Of these, butyric acid is particularly preferred.

Another member of the anti-cancer agent sensitivity determination marker of the present invention is triethanolamine or a substance involved in triethanolamine metabolism (also called a triethanolamine-metabolism-related substance). The substance encompasses triethanolamine and all the substances that can vary the triethanolamine level in the metabolism thereof. Examples of such metabolism-related substances include a substance which promotes metabolism to triethanolamine, a substance which inhibits metabolism to triethanolamine, a substance which promotes metabolism from triethanolamine, and a substance which inhibits metabolism from triethanolamine. Of these, triethanolamine is particularly preferred.

Another member of the anti-cancer agent sensitivity determination marker of the present invention is 1-methylnicotinamide or a substance involved in 1-methylnicotinamide metabolism (also called a 1-methylnicotinamide-metabolism-related substance). The substance encompasses 1-methylnicotinamide and all the substances that can vary the 1-methylnicotinamide level in the metabolism thereof. Examples of such metabolism-related substances include a substance which promotes metabolism to 1-methylnicotinamide, a substance which inhibits metabolism to 1-methylnicotinamide, a substance which promotes metabolism from 1-methylnicotinamide, and a substance which inhibits metabolism from 1-methylnicotinamide. Of these, 1-methylnicotinamide is particularly preferred.

Another member of the anti-cancer agent sensitivity determination marker of the present invention is NADH or a substance involved in NADH metabolism (also called an NADH-metabolism-related substance). The substance encompasses NADH and all the substances that can vary the NADH level in the metabolism thereof. Examples of such metabolism-related substances include a substance which promotes metabolism to NADH, a substance which inhibits metabolism to NADH, a substance which promotes metabolism from NADH, and a substance which inhibits metabolism from NADH. Of these, NADH is particularly preferred.

Another member of the anti-cancer agent sensitivity determination marker of the present invention is $NAD^+$ or a substance involved in $NAD^+$ metabolism (also called an $NAD^+$-metabolism-related substance). The substance encompasses $NAD^+$ and all the substances that can vary the $NAD^+$ level in the metabolism thereof. Examples of such metabolism-related substances include a substance which promotes metabolism to $NAD^+$, a substance which inhibits metabolism to $NAD^+$, a substance which promotes metabolism from $NAD^+$, and a substance which inhibits metabolism from $NAD^+$. Of these, $NAD^+$ is particularly preferred.

Among the aforementioned anti-cancer agent sensitivity determination markers, Asp, N,N-dimethylglycine, γ-Glu-Cys, glutathione, GABA, 1-methyladenosine, spermine, spermidine, 7,8-dihydrobiopterin, and 1-methylnicotinamide were previously confirmed, by the present inventors, to serve as markers that can determine sensitivity of a cancer patient to irinotecan or SN-38. The present inventors have newly found that these compounds can serve as markers that can determine sensitivity of a cancer patient to anti-cancer agents including 5-FU and L-OHP.

As shown in the Examples described hereinbelow, Asp, Gly, Arg, N-acetyl-β-alanine, N-acetylornithine, cadaverine, cysteic acid, 2-aminoadipic acid, γ-Glu-Cys, β-Ala-Lys, Glu-Glu, S-lactoylglutathione, guanosine, CMP, UMP, 1-methyladenosine, UDP, CTP, sedoheptulose 7-phosphate, dihydroxyacetone phosphate, 2,3-diphosphoglyceric acid, pyruvic acid, malic acid, $N^1$-acetylspermine, N-acetylputrescine, $N^8$-acetylspermidine, putrescine, spermine, spermidine, 7,8-dihydrobiopterin, and 6-phosphogluconic acid exhibited a considerable intracellular level increase in HCT116 cells, which are high sensitivity cells, after exposure to 5-FU/L-OHP. In contrast, in DLD-1 cells, which are low sensitivity cells, these substances exhibited an intracellular level variation that was not so considerable, as compared with the case of HCT116 cells, or exhibited a drop in intracellular level as compared with a control group. Therefore, these substances are useful as markers for determining sensitivity of a cancer patient to an anti-cancer agent including 5-FU and L-OHP.

As shown in the Examples described hereinbelow, N,N-dimethylglycine, 3-methylhistidine, $N^5$-ethylglutamine, glutathione, dATP, butyric acid, triethanolamine, and 1-methylnicotinamide exhibited a considerable intracellular level increase in DLD-1 cells, which are low sensitivity cells, after exposure to 5-FU/L-OHP. In contrast, in HCT116 cells, which are high sensitivity cells, these substances exhibited an intracellular level variation that was not so considerable, as compared with the case of DLD-1 cells, or exhibited a drop in intracellular level as compared with a control group. Therefore, these substances are useful as markers for determining sensitivity of a cancer patient to an anti-cancer agent including 5-FU and L-OHP.

As shown in the Examples described hereinbelow, cysteine-glutathione, adenine, and PRPP exhibited a considerable intracellular level drop in HCT116 cells, which are high sensitivity cells, after exposure to 5-FU/L-OHP. In contrast, in DLD-1 cells, which are low sensitivity cells, these substances exhibited an intracellular level variation that was not so considerable, as compared with the case of HCT116 cells, or exhibited an intracellular level increase, as compared with a control group. Therefore, these substances are useful as markers for determining sensitivity of a cancer patient to an anti-cancer agent including 5-FU and L-OHP.

As shown in the Examples described hereinbelow, NADH and $NAD^+$ exhibited a considerable intracellular level drop in DLD-1 cells, which are low sensitivity cells, after exposure to 5-FU/L-OHP. In contrast, in HCT116 cells, which are high sensitivity cells, these substances exhibited an intracellular level variation that was not so considerable, as compared with the case of DLD-1 cells. Therefore, these substances are useful as markers for determining sensitivity of a cancer patient to an anti-cancer agent including 5-FU and L-OHP.

As shown in the Examples described hereinbelow, GABA exhibited a considerable intracellular level increase in HCT116 cells, which are high sensitivity cells, after exposure to 5-FU/L-OHP. In contrast, in DLD-1 cells, which are low sensitivity cells, GABA exhibited an intracellular level variation that was not so considerable, as compared with the case of HCT116 cells. Also, the GABA level before drug treatment was found to be higher in low-sensitivity DLD-1 cells than in high-sensitivity HCT116 cells. In addition the blood GABA level was found to be high in colorectal patients who have poor therapeutic response to the mFOL-FOX6-bevacizumab combination therapy. Therefore, GABA is useful as a marker for determining sensitivity of a cancer patient to an anti-cancer agent including 5-FU and L-OHP.

As described above, oxaliplatin and a salt thereof, and fluorouracil and a salt thereof are examples of the anti-cancer agent to which the sensitivity determination marker of the present invention is applied. However, in addition to oxaliplatin and fluorouracil, an anti-cancer agent that is metabolized in the body, to thereby being transformed to oxaliplatin or fluorouracil may be the anti-cancer agent sensitivity determination marker of the present invention is applied. Specifically, tegaful and capecitabine are known to be metabolized in the body, to thereby form fluorouracil. Thus, instead of fluorouracil, tegaful or capecitabine may be used as a target of the anti-cancer agent sensitivity determination marker of the present invention is applied. In this case, an anti-cancer agent including oxaliplatin or a salt thereof and tegaful or a salt thereof, and an anti-cancer agent including oxaliplatin or a salt thereof and capecitabine or a salt thereof are targets of the anti-cancer agent sensitivity determination marker of the present invention.

The anti-cancer agent to which the anti-cancer agent sensitivity determination marker of the present invention is applied is an anti-cancer agent including oxaliplatin or a salt thereof and fluorouracil or a salt thereof. No particular limitation is imposed on the additional anti-cancer agent used in combination with the target anti-cancer agent of the present invention. Examples of the additional anti-cancer agent include cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, uracil, doxifluridine, gimeracil/oteracil, cytarabine, enocitabine, gemcitabine, 6-mercaptopurine, fuludarabin, pentostatin, cladribine, hydroxyurea, doxorubicin, epirubicin, daunorubicin, idarubicine, pirarubicin, mitoxantrone, amurubicin, actinomycin D, bleomycine, pepleomycin, mytomycin C, aclarubicin, zinostatin, vincristine, vindesine, vinblastine, vinorelbine, paclitaxel, docetaxel, irinotecan, irinotecan active metabolite (SN-38), nogitecan, topotecan, etoposide, prednisolone, dexamethasone, tamoxifen, toremifene, medroxyprogesterone, anastrozole, exemestane, letrozole, rituximab, imatinib, gefitinib, gemtuzumab-ozogamicin, bortezomib, erlotinib, cetuximab, bevacizumab, sunitinib, sorafenib, dasatinib, panitumumab, asparaginase, tretinoin, arsenic trioxide, folinate, levofolinate, salts thereof, and active metabolites of any of these. Of these, combinations of the target anti-cancer agent with one or more members selected from among irinotecan, SN-38, cetuximab, bevacizumab, dasatinib, panitumumab, folinate, and levofolinate are preferred, with combinations of the target anti-cancer agent with one or more members selected from among irinotecan, cetuximab, bevacizumab, folinate, and levofolinate being particularly preferred. In the case where an anti-cancer agent including oxaliplatin or a salt thereof and fluorouracil or a salt thereof is combined with an additional anti-cancer agent, examples of the anti-cancer agent include levofolinate, folinate, levofolinate and bevacizumab, folinate and bevacizumab, levofolinate and cetuximab, folinate and cetuximab, and irinotecan.

In order to determine the anti-cancer agent sensitivity of a specimen by use of the anti-cancer agent sensitivity determination marker of the present invention, the level of any of these metabolism-related substances present in the specimen can be measured. Examples of the specimen include bio-samples derived from subjects having cancer (i.e., cancer patients) such as blood, serum, plasma, urine, tumor tissue and cells, ascites, pleural effusion, cerebrospinal fluid, feces, and sputum. Of these, serum is particularly preferred.

Examples of the target cancer of the present invention include lip, oral, pharyngeal cancers such as pharyngeal cancer; gastrointestinal tract cancers such as esophageal cancer, gastric cancer, and colorectal cancer; respiratory and pleural organ cancers such as lung cancer; bone cancer and articular cartilage cancer; skin melanoma, squamous cell cancer, and other skin cancers; mesothelial and soft tissue cancer such as mesothelioma; female venereal cancers such as breast cancer, uterine cancer, and ovarian cancer; male venereal cancers such as prostatic cancer; urinary tract cancer such as bladder cancer; eye, brain, and central nerve cancers such as brain tumor; thyroid and endocrine cancer; lymphoid tissue, hematogeneous tissue, and related tissue cancers such as non-Hodgkin lymphoma and lymphocytic leukemia; and metastatic cancers from these cancers as primary lesions. The present invention is particularly preferably applied to non-small-cell lung cancer, small-cell lung cancer, cervical cancer, ovarian cancer, gastric cancer, colorectal cancer, squamous cell cancer, and malignant lymphoma.

The means for determining these metabolism-related substances present in a specimen may be appropriately selected in accordance with the substance to be determined. Examples of the determination means include mass spectrometers (e.g., CE-TOFMS and gas chromatography-mass spectrometry (GC-MS)), HPLC, immunological assay, and biological assay.

In the case where any of Asp, Gly, Arg, N-acetyl-β-alanine, N-acetylornithine, cadaverine, cysteic acid, 2-aminoadipic acid, γ-Glu-Cys, β-Ala-Lys, Glu-Glu, S-lactoylglutathione, guanosine, CMP, UMP, 1-methyladenosine, UDP, CTP, sedoheptulose 7-phosphate, dihydroxyacetone phosphate, 2,3-diphosphoglyceric acid, pyruvic acid, malic acid, $N^1$-acetylspermine, N-acetylputrescine, $N^8$-acetylspermidine, putrescine, spermine, spermidine, 7,8-dihydrobiopterin, and 6-phosphogluconic acid is used, and the sensitivity of a patient to the target anti-cancer agent is determined as follows. The level of any of these metabolism-related substances present in a bio-sample derived from the cancer patient is measured before and after administration of the anti-cancer agent. When the metabolism-related substance level increases or exceeds a predetermined standard level, after administration of the anti-cancer agent, the cancer is determined to have sensitivity to the anti-cancer agent, whereas when the substance level is constant or below a specific standard level, after administration of the anti-cancer agent, the cancer is determined to have no sensitivity to the anti-cancer agent.

When the cancer has no sensitivity to an anti-cancer agent, no pharmacological effect can be expected from the anti-cancer agent. If such a pharmaceutically impotent anti-cancer agent is continuously administered to the patient, the cancer may progress, and side effects may be aggravated. Thus, the anti-cancer agent sensitivity determination marker of the present invention may be employed not only to determine therapeutic response to the anti-cancer agent, but also to greatly contribute to prevention of aggravation of side effects, which would otherwise be caused by continuous administration of a pharmaceutically impotent anti-cancer agent.

In the case where any of N,N-dimethylglycine, 3-methylhistidine, $N^5$-ethylglutamine, glutathione, dATP, butyric acid, triethanolamine, and 1-methylnicotinamide is used, the sensitivity of a cancer patient to the anti-cancer agent is determined as follows. The level of any of these metabolism-related substances present in a bio-sample derived from the cancer patient is measured before and after administration of the anti-cancer agent. When the metabolism-related substance level increases or exceeds a predetermined standard level, after administration of the anti-cancer agent, the cancer is determined to have no sensitivity to the anti-cancer agent, whereas when the substance level is constant or below a specific standard level, after administration of the anti-cancer agent, the cancer is determined to have sensitivity to the anti-cancer agent.

When the cancer has no sensitivity to an anti-cancer agent, no pharmacological effect can be expected from the anti-cancer agent. If such a pharmaceutically impotent anti-cancer agent is continuously administered to the patient, the cancer may progress, and side effects may be aggravated. Thus, the anti-cancer agent sensitivity determination marker of the present invention may be employed not only to determine therapeutic response to the anti-cancer agent, but also to greatly contribute to prevention of aggravation of side effects, which would otherwise be caused by continuous administration of a pharmaceutically impotent anti-cancer agent.

In the case where any of cysteine-glutathione, adenine, and PRPP is used, the sensitivity of a cancer patient to the anti-cancer agent is determined as follows. The level of any of these metabolism-related substances present in a bio-sample derived from the cancer patient is measured before and after administration of the anti-cancer agent. When the metabolism-related substance level decreases or is below a predetermined standard level, after administration of the anti-cancer agent, the cancer is determined to have sensitivity to the anti-cancer agent, whereas when the substance level is constant or exceeds a specific standard level, after administration of the anti-cancer agent, the cancer is determined to have no sensitivity to the anti-cancer agent.

When the cancer has no sensitivity to an anti-cancer agent, no pharmacological effect can be expected from the anti-cancer agent. If such a pharmaceutically impotent anti-cancer agent is continuously administered to the patient, the cancer may progress, and side effects may be aggravated. Thus, the anti-cancer agent sensitivity determination marker of the present invention may be employed not only to determine therapeutic response to the anti-cancer agent, but also to greatly contribute to prevention of aggravation of side effects, which would otherwise be caused by continuous administration of a pharmaceutically impotent anti-cancer agent.

In the case where any of NADH and $NAD^+$ is used, the sensitivity of a cancer patient to the anti-cancer agent is determined as follows. The level of any of these metabolism-related substances present in a bio-sample derived from the cancer patient is measured before and after administration of the anti-cancer agent. When the metabolism-related substance level decreases or is below a predetermined standard level, after administration of the anti-cancer agent, the cancer is determined to have no sensitivity to the anti-cancer agent, whereas when the substance level is constant or exceeds a specific standard level, after administration of the anti-cancer agent, the cancer is determined to have sensitivity to the anti-cancer agent.

When the cancer has no sensitivity to an anti-cancer agent, no pharmacological effect can be expected from the anti-cancer agent. If such a pharmaceutically impotent anti-cancer agent is continuously administered to the patient, the cancer may progress, and side effects may be aggravated. Thus, the anti-cancer agent sensitivity determination marker of the present invention may be employed not only to determine therapeutic response to the anti-cancer agent, but also to greatly contribute to prevention of progression of cancer and aggravation of side effects, which would otherwise be caused by continuous administration of a pharmaceutically impotent anti-cancer agent.

In the case where GABA is used, the sensitivity of a cancer patient to the anti-cancer agent is determined as follows. The GABA level of a bio-sample derived from the cancer patient is measured before and after administration of the anti-cancer agent. When the metabolism-related substance level increases or exceeds a predetermined standard level, after administration of the anti-cancer agent, the cancer is determined to have sensitivity to the anti-cancer agent, whereas when the substance level is constant or below a specific standard level, after administration of the anti-cancer agent, the cancer is determined to have no sensitivity to the anti-cancer agent. Furthermore, before administration of the anti-cancer agent, or before administration of the anti-cancer agent in each therapy cycle, when the GABA level is higher than a predetermined standard level, the cancer is determined to have no sensitivity to the anti-cancer agent.

When the cancer has no sensitivity to an anti-cancer agent, no pharmacological effect can be expected from the anti-cancer agent. If such a pharmaceutically impotent anti-cancer agent is continuously administered to the patient, the cancer may progress, and side effects may be aggravated. Thus, the anti-cancer agent sensitivity determination marker of the present invention may be employed not only to determine therapeutic response to the anti-cancer agent, but also to greatly contribute to prevention of aggravation of side effects, which would otherwise be caused by continuous administration of a pharmaceutically impotent anti-cancer agent.

In order to carry out the method of the present invention for determining sensitivity of a specimen to an anti-cancer agent, preferably, a kit containing a protocol for measuring any of the metabolism-related substances present in the specimen is employed. The kit contains a reagent for measuring any of these metabolism-related substances, an indication of an instruction manual for use of the reagent, standards for determining the presence or absence of sensitivity to the anti-cancer agent, etc. The standards include (relative) standard levels of these metabolism-related substances, a (relative) high threshold level, a (relative) low threshold level, factors affecting the measurements, the degree of the effects, etc. These substance levels may be set so as to suit the target anti-cancer agent selected. The sensitivity determination may be performed in the same manner on the basis of the standards.

In the case where any of Asp, Gly, Arg, N-acetyl-β-alanine, N-acetylornithine, cadaverine, cysteic acid, 2-aminoadipic acid, γ-Glu-Cys, β-Ala-Lys, Glu-Glu, S-lactoylglutathione, guanosine, CMP, UMP, 1-methyladenosine, UDP, CTP, sedoheptulose 7-phosphate, dihydroxyacetone phosphate, 2,3-diphosphoglyceric acid, pyruvic acid, malic acid, $N^1$-acetylspermine, N-acetylputrescine, $N^8$-acetylspermidine, putrescine, spermine, spermidine, 7,8-dihydrobiopterin, and 6-phosphogluconic acid is used, screening of an anti-cancer agent sensitivity enhancer can be performed through employment, as an index, of variation in expression of any of the substances after exposure to the anti-cancer agent, specifically, promotion of the variation or increase in level. That is, a substance which promotes variation in expression of any of Asp, Gly, Arg, N-acetyl-β-alanine, N-acetylornithine, cadaverine, cysteic acid, 2-aminoadipic acid, γ-Glu-Cys, β-Ala-Lys, Glu-Glu, S-lactoylglutathione, guanosine, CMP, UMP, 1-methyladenosine, UDP, CTP, sedoheptulose 7-phosphate, dihydroxyacetone phosphate, 2,3-diphosphoglyceric acid, pyruvic acid, malic acid, $N^1$-acetylspermine, N-acetylputrescine, $N^8$-acetylspermidine, putrescine, spermine, spermidine, 7,8-dihydrobiopterin, and 6-phosphogluconic acid or which increases the metabolism-related substance level, in vitro or in vivo after exposure to the anti-cancer agent, enhances the sensitivity to the anti-cancer agent. For example, in an in vitro case, a substance which promotes variation in expression of any of Asp, Gly, Arg, N-acetyl-β-alanine, N-acetylornithine, cadaverine, cysteic acid, 2-aminoadipic acid, γ-Glu-Cys, β-Ala-Lys, Glu-Glu, S-lactoylglutathione, guanosine, CMP, UMP, 1-methyladenosine, UDP, CTP, sedoheptulose 7-phosphate, dihydroxyacetone phosphate, 2,3-diphosphoglyceric acid, pyruvic acid, malic acid, $N^1$-acetylspermine, N-acetylputrescine, $N^8$-acetylspermidine, putrescine, spermine, spermidine, 7,8-dihydrobiopterin, and 6-phosphogluconic acid present in cells or which increases the metabolism-related substance level after exposure to an anti-cancer agent can serve as a substance which enhances the sensitivity to the anti-cancer agent (i.e., anti-cancer agent sensitivity enhancer). Also, in an in vivo case, a substance which promotes variation in expression of any of Asp, Gly, Arg, N-acetyl-β-alanine, N-acetylornithine, cadaverine, cysteic acid, 2-aminoadipic acid, γ-Glu-Cys, β-Ala-Lys, Glu-Glu, S-lactoylglutathione, guanosine, CMP, UMP, 1-methyladenosine, UDP, CTP, sedoheptulose 7-phosphate, dihydroxyacetone phosphate, 2,3-diphosphoglyceric acid, pyruvic acid, malic acid, $N^1$-acetylspermine, N-acetylputrescine, $N^8$-acetylspermidine, putrescine, spermine, spermidine, 7,8-dihydrobiopterin, and 6-phosphogluconic acid present in a cancer-bearing animal or a substance which increases the metabolism-related substance level, after exposure to an anti-cancer agent, can serve as a substance which enhances the sensitivity to the anti-cancer agent (i.e., anti-cancer agent sensitivity enhancer).

In the case where any of N,N-dimethylglycine, 3-methylhistidine, $N^5$-ethylglutamine, glutathione, dATP, butyric acid, triethanolamine, and 1-methylnicotinamide is used, screening of an anti-cancer agent sensitivity enhancer can be performed through employment, as an index, of variation in expression of any of the substances after exposure to the anti-cancer agent. That is, a substance which suppresses variation in expression of N,N-dimethylglycine, 3-methylhistidine, $N^5$-ethylglutamine, glutathione, dATP, butyric acid, triethanolamine, and 1-methylnicotinamide, in vitro or in vivo after exposure to the anti-cancer agent, enhances the sensitivity to the anti-cancer agent. For example, in an in vitro case, a substance which suppresses variation in expression of N,N-dimethylglycine, 3-methylhistidine, $N^5$-ethylglutamine, glutathione, dATP, butyric acid, triethanolamine, and 1-methylnicotinamide present in cells after exposure to an anti-cancer agent can serve as a substance which enhances the sensitivity to the anti-cancer agent (i.e., anti-cancer agent sensitivity enhancer). Also, in an in vivo case, a substance which suppresses variation in expression of N,N-dimethylglycine, 3-methylhistidine, $N^5$-ethylglutamine, glutathione, dATP, butyric acid, triethanolamine, and 1-methylnicotinamide present in a cancer-bearing animal, after exposure to an anti-cancer agent, can serve as a substance which enhances the sensitivity to the anti-cancer agent (i.e., anti-cancer agent sensitivity enhancer).

In the case where any of cysteine-glutathione, adenine, and PRPP is used, screening of an anti-cancer agent sensitivity enhancer can be performed through employment, as an index, of variation in expression of any of the substances after exposure to the anti-cancer agent, specifically, promotion of the variation or decrease in the substance level. That is, a substance which promotes the variation of cysteine-glutathione, adenine, and PRPP or which decreases the substance level, in vitro or in vivo after exposure to the anti-cancer agent, enhances the sensitivity to the anti-cancer agent. For example, in an in vitro case, a substance which promotes the variation of cysteine-glutathione, adenine, and PRPP or which decreases the substance level in cells after exposure to an anti-cancer agent can serve as a substance which enhances the sensitivity to the anti-cancer agent (i.e., anti-cancer agent sensitivity enhancer). Also, in an in vivo case, a substance which promotes the variation cysteine-glutathione level, adenine level, and PRPP level of a cancer-bearing animal or a substance which decreases the substance level, after exposure to an anti-cancer agent, can serve as a substance which enhances the sensitivity to the anti-cancer agent (i.e., anti-cancer agent sensitivity enhancer).

In the case where any of NADH and $NAD^+$ is used, screening of an anti-cancer agent sensitivity enhancer can be performed through employment, as an index, of variation in expression of any of the substances after exposure to the anti-cancer agent. That is, a substance which suppresses variation in expression of NADH and $NAD^+$, in vitro or in vivo after exposure to the anti-cancer agent, enhances the sensitivity to the anti-cancer agent. For example, in an in vitro case, a substance which suppresses variation in expression of NADH and $NAD^+$ in cells after exposure to an anti-cancer agent can serve as a substance which enhances the sensitivity to the anti-cancer agent (i.e., anti-cancer agent sensitivity enhancer). Also, in an in vivo case, a substance which suppresses variation in expression of NADH and $NAD^+$ present in a cancer-bearing animal, after exposure to an anti-cancer agent, can serve as a substance which enhances the sensitivity to the anti-cancer agent (i.e., anti-cancer agent sensitivity enhancer).

In the case where GABA is used, screening of an anti-cancer agent sensitivity enhancer can be performed through employment, as an index, of variation in expression of GABA after exposure to the anti-cancer agent. That is, a substance which decreases the GABA level before exposure to the anti-cancer agent or which promotes variation in the expression or elevates the level after exposure to the anti-cancer agent, in vitro or in vivo, enhances the sensitivity to the anti-cancer agent. For example, in an in vitro case, a substance which decreases the intracellular GABA level after exposure to the anti-cancer agent, in the case where cancer cells have been treated with a substance before exposure to the anti-cancer agent, can serve as a substance which enhances the sensitivity to the anti-cancer agent (i.e., anti-cancer agent sensitivity enhancer). In addition, in an in vitro case, a substance which promotes variation in the expression or elevates the level after exposure to the anti-cancer agent corresponding to the target cancer cells can serve as a substance which enhances the sensitivity to the anti-cancer agent (i.e., anti-cancer agent sensitivity enhancer). Also, in an in vivo case, a substance which decreases the GABA level of a cancer-bearing animal before exposure to the anti-cancer agent or which promotes variation in the GABA expression or elevates the GABA level after exposure to the anti-cancer agent can serve as a substance which enhances the sensitivity to the anti-cancer agent (i.e., anti-cancer agent sensitivity enhancer).

Screening of an anti-cancer agent can be performed by means of the anti-cancer agent sensitivity determination marker of the present invention as an index. That is, a substance which can vary the level of the anti-cancer agent sensitivity determination marker in vitro or in vivo is evaluated as an anti-cancer agent. For example, in an in vitro case, a substance which varies the anti-cancer agent sensitivity determination marker level in various cancer cells after exposure to the substance can serve as an anti-cancer agent. Also, when the anti-cancer agent sensitivity determination marker level in a cancer-bearing animal is varied after administration of a substance thereto, the substance can serve as an anti-cancer agent. If the anti-cancer agent is expected to exhibit a pharmacological effect, the increase in anti-cancer agent sensitivity determination marker level is observed before occurrence of tumor shrinkage or attaining cytocidal effect. Therefore, screening based on the anti-cancer agent sensitivity determination marker level as an index can realize, for a shorter period of time, determination whether or not the test substance serves as a useful anti-cancer agent, whereby efforts and cost involved in the development of anti-cancer agents are greatly expected to be reduced.

Through employment, in combination, of the thus-obtained anti-cancer agent sensitivity enhancer and an anti-cancer agent which is a sensitivity enhancement target of the enhancer, the therapeutic effect of the anti-cancer agent is drastically enhanced. The combination of the anti-cancer agent sensitivity enhancer and the anti-cancer agent which is a sensitivity enhancement target of the enhancer may be a composition containing both ingredients, or a combined drug of preparations containing individual ingredients. These two ingredients may be administered through different routes. The anti-cancer agent to which the anti-cancer agent sensitivity determination marker of the present invention is applied is an anti-cancer agent including oxaliplatin or a salt thereof and fluorouracil or a salt thereof. No particular limitation is imposed on the additional anti-cancer agent used in combination with the target anti-cancer agent of the present invention. Examples of the additional anti-cancer agent include cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, uracil, doxifluridine, gimeracil/oteracil, cytarabine, enocitabine, gemcitabine, 6-mercaptopurine, fuludarabin, pentostatin, cladribine, hydroxyurea, doxorubicin, epirubicin, daunorubicin, idarubicine, pirarubicin, mitoxantrone, amurubicin, actinomycin D, bleomycine, pepleomycin, mytomycin C, aclarubicin, zinostatin, vincristine, vindesine, vinblastine, vinorelbine, paclitaxel, docetaxel, irinotecan, irinotecan active metabolite (SN-38), nogitecan, topotecan, etoposide, prednisolone, dexamethasone, tamoxifen, toremifene, medroxyprogesterone, anastrozole, exemestane, letrozole, rituximab, imatinib, gefitinib, gemtuzumab-ozogamicin, bortezomib, erlotinib, cetuximab, bevacizumab, sunitinib, sorafenib, dasatinib, panitumumab, asparaginase, tretinoin, arsenic trioxide, folinate, levofolinate, salts thereof, and active metabolites of any of these. Of these, combinations of the target anti-cancer agent with one or more members selected from among irinotecan, SN-38, cetuximab, bevacizumab, dasatinib, panitumumab, folinate, and levofolinate are preferred, with combinations of the target anti-cancer agent with one or more members selected from among irinotecan, cetuximab, bevacizumab, folinate, and levofolinate being particularly preferred. In the case where an anti-cancer agent including oxaliplatin or a salt thereof and fluorouracil or a salt thereof is combined with an additional anti-cancer agent, examples of the anti-cancer agent include levofolinate, folinate, levofolinate and bevacizumab, folinate and bevacizumab, levofolinate and cetuximab, folinate and cetuximab, and irinotecan.

EXAMPLES

The present invention will next be described in more detail by way of examples, which should not be construed as limiting the invention thereto.

Example 1

(1) Method
(a) Cells Employed

Two human colorectal cancer cell lines (high-sensitivity: HCT116, low-sensitivity: DLD-1) were employed. HCT116 was obtained from Kabushiki Kaisha Yakult Honsha, and DLD-1 was obtained from Dainippon Sumitomo Pharma Co., Ltd. Cell culturing was performed by means of a ϕ100 mm/Tissue Culture Dish (IWAKI) with a Dulbecco's modified Eagle's Medium (DMEM) containing 10% fetal bovine serum (product of Invitrogen) at 37° C. under 5% $CO_2$ conditions.

(b) Drugs

L-OHP powder was obtained from Kabushiki Kaisha Yakult Honsha. 5-FU powder was obtained from Sigma Aldrich Japan K.K.

(c) Exposure to 5-FU/L-OHP and Recovery of Metabolites in the Cells

The two colorectal cancer cells were exposed to L-OHP by changing the culture medium to a medium containing 100 μmol/L 5-FU and 10 μmol/L L-OHP (employing an anti-cancer agent-free medium as a control group). After exposure to 5-FU/L-OHP (0 hr, 4 hr, 12 hr, 24 hr, and 48 hr), the cells were washed on ice with 5% mannitol (4° C.). Immediately thereafter, methanol (4° C., containing an internal standard) was added to the washed cells, to thereby deactivate present enzymes, and the cells were stored at −80° C. Separately, cells for cell count were provided in addition to the cells from which metabolites were extracted, and then subjected to the same treatment before performing cell count. The data were employed in correction of the cell counts.

(d) Preparation of Metabolomic Sample

Chloroform and Milli-Q water were added to the methanol solution stored at −80° C., and liquid-liquid extraction was performed, to thereby removed miscellaneous matters. A water-methanol layer containing metabolites was recovered and filtered through an ultrafiltration membrane (fraction molecular weight: 5,000 Da), to thereby remove protein. The filtrate was dried under reduced pressure and then stored at −80° C. The filtrate was dissolved in Milli-Q water, and immediately after, the solution was subjected to metabolomic analysis.

(e) Metabolomic Analysis

Comprehensive analysis of intercellular metabolites was performed by means of a capillary electrophoresis-time-of-flight-type mass spectrometer (CE-TOFMS) (product of Agilent Technologies). In the comprehensive analysis of cationic metabolites, voltage was applied so that the outlet of the capillary served as a negative electrode, whereas in the comprehensive analysis of anionic metabolites, voltage was applied so that the outlet of the capillary served as a positive electrode. Metabolites detected at m/z values of 50 to 1,000 were simultaneously quantitated.

(f) Data Analysis

The peaks of each sample detected through CE-TOFMS were identified with reference to about 500 sample data sets whose m/z values and migration times had been known. The metabolite level was obtained by dividing the peak area of the metabolite by that of the internal standard, and the value was corrected by subtracting therefrom reference sample data.

(2) Results

Human colorectal cancer cells of two cell lines having different sensitivities (high-sensitivity: HCT116, low-sensitivity: DLD-1) were exposed to 5-FU/L-OHP for 24 hours. Thereafter, metabolites which had exhibited variation in metabolomic data were extracted (FIG. 1). As a result, after exposure to 5-FU/L-OHP, a considerable intercellular level rise was observed in high-sensitivity cells with respect to the following metabolites: Asp, Gly, Arg, N-acetyl-β-alanine, N-acetylornithine, cadaverine, cysteic acid, 2-aminoadipic acid, GABA (γ-aminobutyric acid), γ-Glu-Cys, β-Ala-Lys, Glu-Glu, S-lactoylglutathione, guanosine, CMP, UMP, 1-methyladenosine, UDP, CTP, sedoheptulose 7-phosphate, dihydroxyacetone phosphate, 2,3-diphosphoglyceric acid, pyruvic acid, malic acid, $N^1$-acetylspermine, N-acetylputrescine, $N^8$-acetylspermidine, putrescine, spermine, spermidine, 7,8-dihydrobiopterin, and 6-phosphogluconic acid. After exposure to 5-FU/L-OHP, a considerable intercellular level rise was observed in low-sensitivity cells with respect to the following metabolites: N,N-dimethylglycine, 3-methylhistidine, $N^5$-ethylglutamine, glutathione, dATP, butyric acid, triethanolamine, and 1-methylnicotinamide. After exposure to 5-FU/L-OHP, a considerable intercellular level drop was observed in high-sensitivity cells with respect to the following metabolites: cysteine-glutathione, adenine, and PRPP. After exposure to 5-FU/L-OHP, a considerable intercellular level drop was observed in low-sensitivity cells with respect to the following metabolites: NADH and $NAD^+$.

The intracellular GABA level before drug treatment was higher in low-sensitivity cells than in high-sensitivity cells (FIG. 2).

Example 2

Clinical Test of Human Subjects Who Had Received mFOLFOX6-Bevacizumab Combination Therapy 1. Method The tested human subjects were cancer patients who had received a cancer chemotherapy (mFOLFOX6-bevacizumab combination therapy) involving administration, in combination, fluorouracil (400 mg/m$^2$) (via rapid intravenous injection), levofolinate (200 mg/m$^2$), fluorouracil (2,400 mg/m$^2$) (via continuous intravenous infusion), oxaliplatin (85 mg/m$^2$), and bevacizumab (5 mg/kg). Second phase clinical tests were carried out in order to investigate efficacy and safety of the cancer chemotherapy and causes for difference therein between individual patients. The tested patients were inoperable advanced/recurrent cancer patients who had received none of chemotherapy, immunotherapy, and radiotherapy. The human subjects were selected on the basis of the following standards: (1) a case having a histopathologically identified colorectal cancer; (2) a case of an inoperable advanced/recurrent cancer; (3) a case having a detectable lesion; (4) a case who had received none of chemotherapy, immunotherapy, and radiotherapy (but there can be registered a case who had received a post-operative adjuvant therapy by a fluorouracil completed within 6 months from the recurrence-identified day); (5) a case having an age of ≥20; (6) a case having a performance status (ECOG scale) of 0 or 1; (7) a case which is expected to have a predicted survival period of 3 months or longer; (8) a case who has no severe disorder in main functions (bone marrow, liver, kidney, heart, lung, etc.) and who has clinical test results within 14 days before registration (excluding registration day) falling within the following reference ranges: WBC: 4,000/mm$^3$ to 12,000/mm$^3$, Neutro: ≥2,000/mm$^3$, Hb: ≥9.0 g/dL, PLT: ≥100,000/mm$^3$, AST: ≤100 IU/L, ALT: ≤100 IU/L, T-Bil: ≤1.5 mg/dL. CRE: ≤1.5 mg/dL, urine protein: ≤1+ (qualitative), and PT international ratio: ≤1.5; and (9) a patient who himself or herself provided informed consent of participating in a test including a genetic polymorphism test or a proteomic/metabolomic analysis, with the date and signature. Excluded were the following cases: (1) a case who received transfusion or administration of a blood preparation and a hematopoietic factor preparation (e.g., G-CSF) ≤14 days before registration; (2) a case who had experienced sever drug hypersensitivity; (3) a case having a simultaneous cancer and an allochronic cancer with a disease-free period of <5 years; (4) a case having a sensory disorder or dysesthesia; (5) a case having a clinically problematic infection; (6) a case positive to an HBs antigen; (7) a case having a clinically problematic heart disease identified by an ECG or the like within 28 days before registration; (8) a case having interstitial pneumonia or pulmonary fibrosis diagnosed by a simple chest X-ray image or the like; (9) a case having pleural fluid, ascites, or pericardial fluid which requires treatment; (10) a case having diarrhea (including watery stools); (11) a case having apparent brain metastasis or brain metastasis suspected from clinical conditions; (12) a case who had experienced having thromboembolism in the past; (13) a case who had received laparotomy or intestinal resection ≤28 days before registration, or who had received provision of stoma, biopsy with an incision, or traumatonesis ≤14 days before registration; (14) a case under administration of a platelet function suppressor (an aspirin preparation or an NSAID); (15) a case having insufficiently controlled digestive tract ulcer; (16) a case who had experienced perforation of the digestive tract in the past ≤12 months; (17) a case having insufficiently controlled hypertension; (18) a case having insufficiently controlled diabetes; (19) a case under administration of a cardiac glycoside; (20) a case having a complication of a mental disease or condition who has difficulty in participating in the test; (21) a female subject in pregnancy or lactation or a male or female subject wishing to have a baby or to refuse contraception; and (22) a case who has been judged by a clinical investigator to be unsuited for evaluation of efficacy and safety of the test. In the regimen employed in the test, bevacizumab, oxaliplatin, fluorouracil (via rapid intravenous injection), and levofolinate were administered on day 1 of each cycle, and also fluorouracil was administered via continuous intravenous infusion from day 1 to day 3. Each cycle consisted of two weeks (14 days), and the cycle was repeated to 24 cycles, so long as a patient deviated from the acceptable standards.

Seventy patients in total participated in the clinical test. Among them, tumor shrinkage effect in the target lesion could be assessed in 68 cases. In each of the 68 cases, a sample required for the retrieval of a drug-reactive biomarker was recovered. Among the 68 cases, 13 of them, whose test therapy had been terminated, were simultaneously subjected to a metabolomic analysis through CE-TOFMS, wherein the metabolomes were contained in serum samples of the patients before drug administration. Extraction and assay of metabolomes, and data analysis were performed in the same manner as employed in Example 1. Therapeutic response of a patient was evaluated on the basis of best overall response (the best effect recorded in a period from start of therapy to aggravation/recurrence).

2. Results

Figure 3:
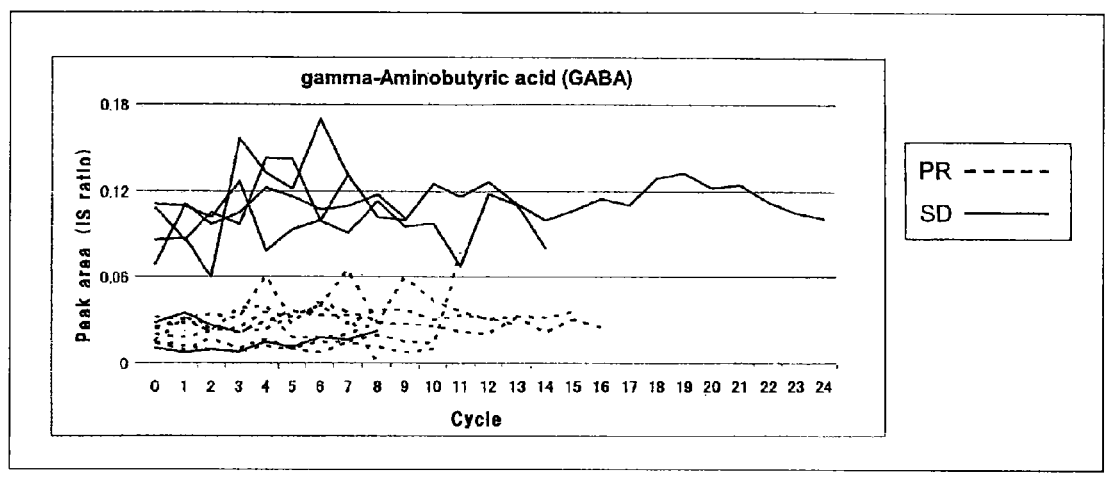
FIG. 3 A graph showing blood GABA levels of patients having different therapeutic responses to the mFOLFOX6-bevacizumab combination therapy, SD denoting stable disease cases, and PR partial response cases.

The tested patients were evaluated in terms of therapeutic response on the basis of best overall response. As a result, among 13 tested cases, there were 6 stable disease (SD) cases and 7 partial response (PR) cases. In each cycle, metabolomes contained in the serum of each patient were comprehensively analyzed through CE-TOFMS before administration of the anti-cancer drug. In all partial response (PR) cases, the blood GABA level was low, whereas in 4 of 6 stable disease (SD) cases, the blood GABA level was high (FIG. 3).

The invention claimed is:

1. A method, comprising
obtaining a first biological sample from a subject having cancer prior to administering an anti-cancer agent comprising oxaliplatin or a salt thereof and fluorouracil or a salt thereof;
administering the anti-cancer agent to the subject;
obtaining a second biological sample from the subject after the administering,
measuring a level of one or more substances selected from the group consisting of Asp, Gly, Arg, N-acetyl-β-alanine, N-acetylornithine, cadaverine, cysteic acid, 2-aminoadipic acid, GABA, γ-Glu-Cys, β-Ala-Lys, Glu-Glu, and S-lactoylglutathione, in the first and second biological samples, and
continue administering the anti-cancer agent to the subject when the level of the one or more substances is increased in the second sample compared to the first sample or discontinuing the administration of the anti-cancer agent when the level of the one or more substances is decreased or unchanged in the second sample compared to the first sample.

2. The method of claim 1, wherein the subject has at least one type of cancer selected from the group consisting of lip, oral, pharyngeal, gastrointestinal tract cancer, esophageal cancer, gastric cancer, colorectal cancer, respiratory cancer, pleural organ cancer, lung cancer, bone cancer, articular cartilage cancer, skin melanoma, squamous cell cancer, other skin cancers, mesothelial and soft tissue, mesothelioma, breast cancer, uterine cancer, ovarian cancer, prostatic cancer, urinary tract cancer, bladder cancer, eye, brain, and central nerve cancers, brain tumor, thyroid and endocrine cancer, lymphoid tissue, hematogeneous tissue, non-Hodgkin lymphoma, lymphocytic leukemia, non-small-cell lung cancer, small-cell lung cancer, cervical cancer, gastric cancer, colorectal cancer, squamous cell cancer, malignant lymphoma and metastatic cancers from these cancers as primary lesions.

3. The method of claim 1 where the measuring comprises measuring with mass spectrometry, high performance liquid chromatography (HPLC), immunological assay, biological assay, or gas chromatography.

* * * * *